US007948621B2

(12) United States Patent
Burns et al.

(10) Patent No.: US 7,948,621 B2
(45) Date of Patent: May 24, 2011

(54) SYSTEMS AND METHODS FOR REMOTE MONITORING OF CONTAMINANTS IN FLUIDS

(75) Inventors: David Burns, Mineral Wells, TX (US); Anhua Mei, Weatherford, TX (US); Mark Scott, Weatherford, TX (US)

(73) Assignee: Perry Equipment Corporation, Mineral Wells, TX (US)

( * ) Notice: Subject to any disclaimer, the term of this patent is extended or adjusted under 35 U.S.C. 154(b) by 344 days.

(21) Appl. No.: 11/823,585

(22) Filed: Jun. 28, 2007

(65) Prior Publication Data
US 2009/0002704 A1 Jan. 1, 2009

(51) Int. Cl.
*G01N 21/00* (2006.01)
(52) U.S. Cl. .................................. 356/338; 356/336
(58) Field of Classification Search .............. 356/342, 356/335–338, 246, 432–444; 250/573, 576, 250/239, 227.25; 422/104, 102, 82.05, 82.09; 385/12, 125
See application file for complete search history.

(56) References Cited

U.S. PATENT DOCUMENTS

| | | | | |
|---|---|---|---|---|
| 3,794,909 A | | 2/1974 | Smith | 324/32 |
| 3,941,479 A | * | 3/1976 | Whitehead | 356/335 |
| 4,413,533 A | * | 11/1983 | Diesel | 73/863.31 |
| 4,809,543 A | | 3/1989 | Baillie | 73/61.1 |
| 5,040,890 A | | 8/1991 | North, Jr. | 356/72 |
| 5,148,945 A | | 9/1992 | Geatz | 222/1 |
| 5,751,422 A | * | 5/1998 | Mitchell | 356/337 |
| 6,062,092 A | | 5/2000 | Weaver | 73/863.03 |
| 6,168,647 B1 | | 1/2001 | Perry, Jr. et al. | 95/19 |
| 6,357,304 B1 | * | 3/2002 | Mayeaux | 73/863.23 |
| 6,584,865 B1 | | 7/2003 | Doherty et al. | 73/863.03 |
| 6,813,303 B2 | | 11/2004 | Matsuda et al. | 372/75 |
| 7,024,867 B2 | | 4/2006 | Arman et al. | 62/6 |
| 2002/0007858 A1 | | 1/2002 | Xu et al. | 137/828 |
| 2003/0235926 A1 | * | 12/2003 | Knollenberg et al. | 436/181 |
| 2004/0079236 A1 | | 4/2004 | Welker | 96/413 |
| 2004/0139785 A1 | | 7/2004 | Abdul-Khalek | 73/28.01 |
| 2005/0151968 A1 | | 7/2005 | Drake et al. | 356/338 |
| 2008/0156073 A1 | * | 7/2008 | Burns et al. | 73/23.35 |

OTHER PUBLICATIONS

PCT International Search Report based on PCT/US07/15138 dated May 29, 2008.

* cited by examiner

*Primary Examiner* — Tarifur Chowdhury
*Assistant Examiner* — Michael LaPage
(74) *Attorney, Agent, or Firm* — Greenberg Traurig, LLP; Chinh H. Pham

(57) ABSTRACT

A system and method of monitoring contaminant particles in pipelines. The system can include a probe for extending into a pipeline, and sampling fluid in the pipeline to ensure that a representative amount of contaminants within the pipeline can subsequently be measured. An analyzer receives the sampled fluid from the probe, illuminates the sampled fluid with a light source, and collects scattered light from any contaminant particles in the illuminated sampled fluid. A detector receives the scattered light from the analyzer, and converts the scattered light into an electrical signal that is proportional to the contaminant particles size. A processor receives the electrical signal from the detector, converts the electrical signal into digital data pertaining to the contaminant particles, and transmits the digital data on an Ethernet connection, or wireless signal to a communication network for distribution to at least one digital data processor for display and evaluation.

43 Claims, 8 Drawing Sheets

SYSTEMS AND METHODS FOR REMOTE MONITORING OF CONTAMINANTS IN FLUIDS

FIELD OF THE INVENTION

The present invention relates to remote monitoring systems, and more particularly to an optical monitoring system designed to remotely monitor contaminant levels in process pipelines.

BACKGROUND

Current commercially available gas turbines and other critical gas or fluid flow systems for use in connection with industrial processes can be extremely sensitive to contamination, such as, solid contaminants (i.e., particulates), liquid contaminants, and/or liquid aerosol, present within the process fluid flow. Solid contaminants, as an example, can act to wear rotating components, foul heat exchangers, contaminate cooling liquids, clog processing equipment, as well as affecting product quality and numerous other processing and equipment problems. Liquid contaminants, on the other hand, can accumulate or coalesce over time, and can, as the volume increases, travel along the sides and bottom of a pipeline and affect the efficiency of the fluid flow. Likewise, liquid aerosol or droplets, although small in mass, can similarly accumulate and build up over time, and have damaging effects on downstream equipment in the fluid flow system.

In order to minimize the occurrence of such contamination, filtration and separation equipment have been employed in connection with these fluid flow systems, so that contaminants present within the fluid flow can be removed therefrom. At present, most manufacturers have developed cleanliness requirement specifications for their process gas flow systems. To accommodate such requirements, modern filters and separators have been designed to remove particulate contaminants with high efficiency. However, the issue with liquid contaminants or liquid aerosols may remain. Moreover, the selection of filtration and separation equipment that can provide adequate removal of the right contaminants can be a difficult task.

In particular, there is available filtration and separation equipment adapted for handling different contaminants in connection with different applications. As a result, unless there is knowledge about the contaminants within the fluid flow, as well as their characteristics, inadequate filtration and separation equipment may be selected, purchased and subsequently installed. The failure to employ optimal or at least appropriate filtration and separation equipment, in many instances, can lead to inadequate removal of the contaminants resulting in damage to downstream equipment, or detrimental effects to product quality. In addition, operational costs of the system can be significantly higher as a result of poor performance caused by insufficient removal of the contaminants.

Even if the appropriate filters and separators may be used, an additional verification step may be needed in order to assure that contamination within the fluid system is being adequately controlled. Presently, most testing of fluid flow contaminants within an energy industry pipeline is accomplished by collecting samples of the fluid flow for subsequent offsite analysis. However, in many instances, a substantially accurate sample may not be available, especially when the sample cannot be isokinetically collected. In other words, if fluid entering the sampling system does not exhibit similar velocity and kinetic energy to the fluid flow in the pressurized process fluid flow, an accurate representation of contaminants within the fluid flow may not be collected. Additionally, at present, the collected sample must either be mailed or transported to a third party laboratory where the sample sits and waits to be measured and analyzed. During this period, the sample can change and the contaminants can often be lost to the sample container.

Moreover, contamination levels within a pipeline can oftentimes rise suddenly and very quickly. For example, aerosol particles can quickly accumulate and reach dangerous levels without being detected in time to avoid damage to expensive equipment. Current contaminant particle detectors typically lack the capability to remotely and continuously monitor the aerosol contaminants in a pipeline, and to provide an immediate notification and alarm upon the contaminant particles reaching a particular threshold level. It should be appreciated that reference to contaminant particles, or "particles" hereafter can include liquid, solid, and aerosol particles.

Accordingly, a need exists for a system that can remotely and continuously monitor contaminant particle levels in fluid flows, and which can generate an alarm upon a threshold level being reached.

SUMMARY OF THE INVENTION

The present invention provides, in one embodiment, a remote contaminant monitoring system that can include a monitor for measuring contaminant levels in a fluid flow in a pipeline, and for generating data pertaining to contaminants in the fluid flow. The system also includes a remotely located data processor in communication with the monitor, so as to receive data from the monitor for evaluation. A second data processor can further be provided in communication with the remotely located data processor for receiving the evaluated data. In an embodiment, the second data processor can be in communication with the monitor.

In another embodiment, the present invention provides a remote contaminant monitoring system, which can include at least one data processor linked to a communication network, and configured to receive data updates and notifications. The system can also include at least one contaminant monitor for continuously monitoring contaminant levels in a fluid flow in a pipeline, and distributing digital data pertaining to contaminants in the fluid flow over the communication network. A remotely located digital data processor can be in communication with the contaminant monitor, and at least one digital data processor via the communication network. The remotely located digital data processor can access the digital data from the communication network, and can transmit data updates and notifications pertaining to the digital data to the at least one digital data processor via the communication network.

In a further embodiment, the present invention provides a pipeline contaminant monitor for remotely monitoring liquid aerosol contaminants in pipelines. The pipeline contaminant monitor can include a probe for extending into a pipeline, and isokinetically sampling fluid in the pipeline to ensure that a representative amount of contaminants within the pipeline can subsequently be measured. The pipeline contaminant monitor can also include an analyzer that can receive a sampled fluid from the probe, illuminate the sampled fluid with a light source, and collect scattered light from contaminant particles in the illuminated sampled fluid. The pipeline contaminant monitor can also include at least one detector for receiving the scattered light from the analyzer, and converting the scattered light into an electrical signal that in an embodiment, can be proportional to the contaminant particles size. The pipeline contaminant monitor can further include a processor for receiving the electrical signal from the detector, and converting the electrical signal into digital data pertaining to the contaminant particles, such as particle distribution and particle size. The processor can then transmit the digital data to a communication network for distribution to at least one digital data processor for display and evaluation.

In another embodiment, the present invention provides an analyzer for use with the pipeline contaminant monitor. The analyzer can include a flow cell having an inlet, an outlet, and a passageway therebetween. In an embodiment, the flow cell can be transparent. The flow cell can receive a sampled fluid from the probe at the inlet, and can direct the sampled fluid through the passageway and out the outlet. The passageway in the flow cell can serve as a sampling space. The flow cell can be made of various transparent materials, for instance, quartz, glass, plastic, sapphire, etc. The analyzer can also include a light source, such as a laser diode, for propagating a focused beam of light at a portion of the passageway containing the sampled fluid, so that scattered light can be generated when contaminant particles are illuminated by contacting the focused beam. The analyzer can include a collection lens assembly for collecting the scattered light, and transferring the scattered light to a detector, such as a photomultiplier tube, for further processing.

In another embodiment, the present invention provides a method of monitoring contaminants in a pipeline. The method includes 1) inserting a probe into a pipeline for isokinetically sampling fluid in the pipeline to ensure that a representative amount of contaminants within the pipeline can subsequently be measured, 2) isokinetically sampling the fluid in the pipeline, 3) illuminating the sampled fluid with a light source, 4) collecting scattered light from particles in the illuminated sampled fluid, 5) converting the scattered light into an electrical signal that can be proportional to the contaminant particle size, 6) processing the electrical signal into digital data pertaining to the contaminant particles, and 7) distributing the digital data via a communication network to at least one digital data processor for display and evaluation.

In another embodiment, the present invention provides a pipeline contaminant monitor that can include 1) a probe for extending into a pipeline for isokinetically sampling fluid in the pipeline to ensure that a representative amount of aerosol contaminants within the pipeline can subsequently be measured, 2) a quartz flow cell having an inlet, an outlet, and a passageway therebetween, in which the sampled fluid can be received at the inlet, and directed through the passageway and out the outlet, 3) a light source, such as a laser diode, for propagating a focused beam of light at a portion of the passageway containing the sampled fluid, so that scattered light can be generated when a contaminant particle contacts the focused beam, and 4) a collection lens for collecting the scattered light and transferring the scattered light to a detector for further processing.

In another embodiment, the present invention provides a pipeline contaminant monitor that can non-isokinetically sample the fluid in the pipeline. Constant non-isokinetic sampling of the fluid in the pipeline can be utilized when necessary to monitor certain types of fluid streams.

DESCRIPTION OF SPECIFIC EMBODIMENTS

Figure 1:
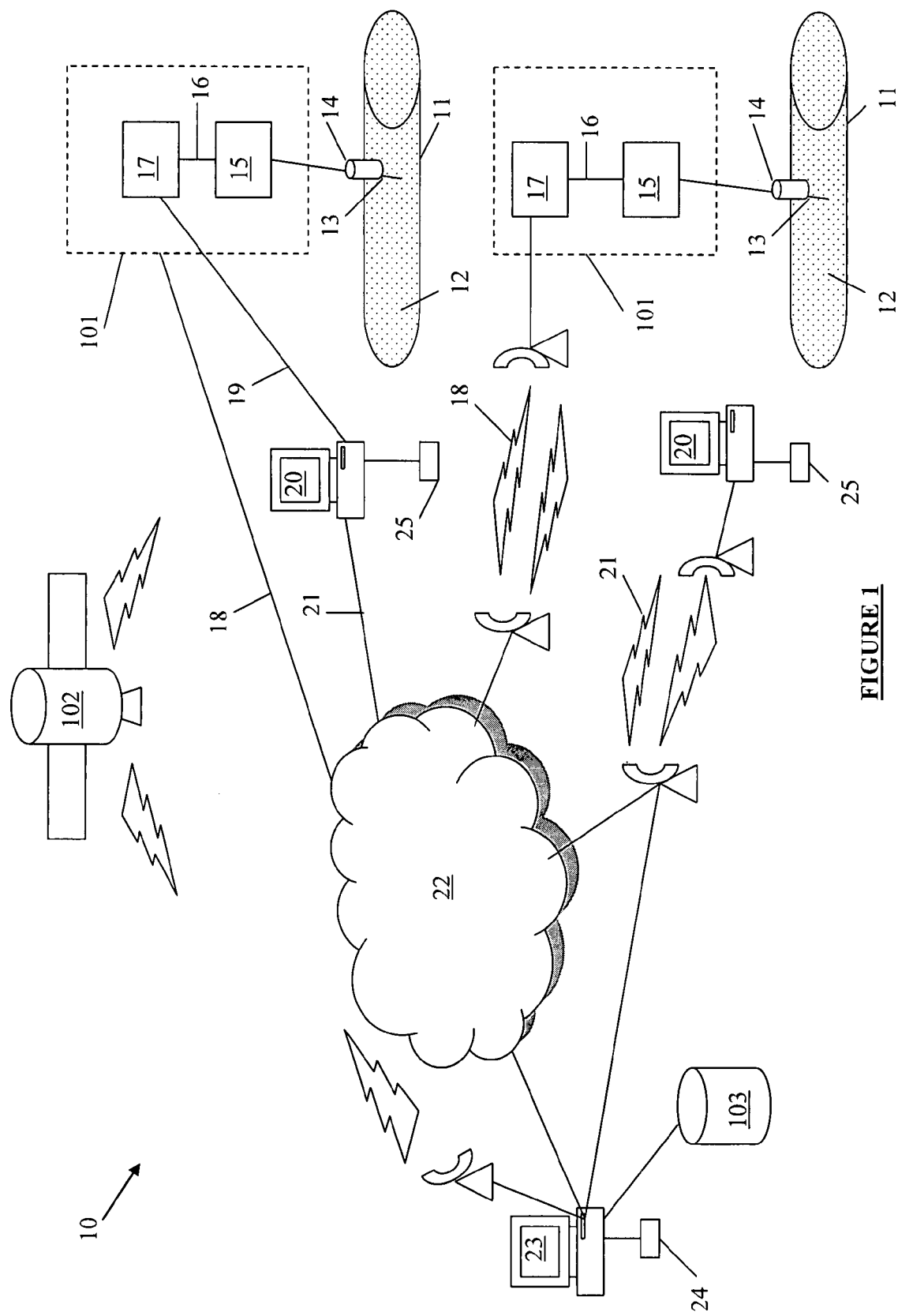
FIG. 1 illustrates an overall system architecture in accordance with one embodiment of the present invention.

Generally, and with reference to FIG. 1, the present invention provides, in one embodiment, a system 10 for use in remotely monitoring contaminants, such as, liquid aerosol particles within a fluid flow system, for instance, pipeline 11. The fluid flow within pipeline 11, in one embodiment may be a high pressure fluid flow. Alternatively, the fluid flow within pipeline 11 can be a low-pressure fluid flow. The overall architecture of system 10 can include a plurality of digital data processors that can be configured in a client-server architecture. For example, a digital data processor, such as central server 23, can be linked via a network 22, e.g., Internet, wireless network, landline, etc. to other digital data processors, such as client server 20 and contaminant monitor 101. Alternatively, central server 23 can be linked to client server 20 and contaminant monitor 101 via a satellite system 102. Of course, other designs and configurations may also be possible.

In an embodiment, the contaminant monitor 101 can be designed to continuously monitor contaminant levels within a fluid flow 12 in a pipeline 11. The contaminants in the fluid flow 12 can include liquid aerosols, liquid mist, solid particles, or hydrocarbon condensate aerosols, and can vary in size. For instance, liquid aerosol particles can range in size from approximately 0.1 microns to about 10 microns. Liquid mist particles can range in size from approximately 11 microns to about 100 microns. The fluid flow 12 in the pipeline 11 on the other hand, can be a liquid, a gas, or can have both liquid and gas components. For example, in an embodiment, the fluid flow 12 can be rich natural gas under high-pressure.

Typically, rich natural gas streams contain components that can condense into liquid form when exposed to pressure and temperature changes. Once in liquid flow, these condensate particles, which can include water and hydrocarbon components, can exist as aerosol particles ranging from about 0.1 to about 10 microns in size. As these aerosols can be volatile, they can vaporize and condense with slight changes in pressure and temperature. In an embodiment, the contaminant monitor 101 can sample and measure the contaminant aerosols at pipeline pressure and temperature as they exist in the pipeline 11. High-pressure can be any pressure above atmospheric pressure. For example, in an embodiment, the fluid flow 12 in pipeline 11 can be pressurized at 2000 PSI (pounds per square inch).

The contaminant monitor 101 can also be designed to send data updates and alarm notifications via network 22 to central server 23 remotely located from pipeline 11. To that end, if the contaminant levels exceed a predetermined threshold, the contaminant monitor 101 can notify the client server 20, and the central server 23 simultaneously. In another embodiment, the contaminant monitor 101 can notify the central server 23 only, which may then notify the client server 20. In either embodiment, the central server 23 can have, for example, unlimited and continuous access to the contaminant monitor 101 and its data. The central server 23 can also store the data pertaining to the fluid flow contaminants in a data store 103, for reference and comparison purposes. For example, to troubleshoot or diagnose problems with pipeline 11.

In addition, the system 10 can provide for notification alerts to be generated when contaminant levels exceed a predetermined threshold. It should be noted that the predetermined threshold can be set to different levels depending on the application. The alerts can then be transmitted from the central server site to the client server site via wireless devices 24, 25. Examples of wireless devices include cell phones, hand-held PDA's, laptop computers, etc.

System 10, in an embodiment, can also include a probe 13 that can be inserted into a pipeline 11 having a fluid flow 12, through an access point, such as valve 14. The probe 13, in an embodiment, can be designed to isokinetically sample gaseous elements, e.g., aerosol particles, of the fluid flow 12. In other words, probe 13 collects the fluid sample at a substantially similar fluid velocity and pressure as that exhibited by the fluid flow in the pipeline 11. The isokinetic method of sampling ensures that the sample can be collected with a contaminant level that is representative of the contaminant level along the pipeline 11. Once collected, the fluid sample can be directed by the probe 13 into the contaminant monitor 101.

In another embodiment, the probe 13 can be designed to non-isokinetically sample the gaseous elements of the fluid flow 12 in the pipeline 11. For example, the probe 13 can collect the fluid sample at a different fluid velocity and pressure as that exhibited by the fluid flow in the pipeline 11. Constant non-isokinetic sampling of the fluid in the pipeline can be utilized when necessary to monitor various types of fluid streams, or for conducting relative data comparisons. Regardless of the sampling method utilized, the fluid sample can be directed by the probe 13 into the contaminant monitor 101.

The contaminant monitor 101, as shown in FIG. 1, can include in one embodiment three subassemblies, an analyzer 15, a fiber optic cable 16, and a processor assembly 17. This configuration is simply one embodiment of the contaminant monitor 101. Those skilled in the art will appreciate that subassemblies 15, 16, and 17 can be combined into a single assembly unit, or fabricated into multiple assemblies. In an embodiment, the contaminant monitor 101 and/or its subassemblies 15, 16, and 17 can be encased in a housing. Depending on the application, the housing (not shown) can, for instance, be a class 1, division 1 or 2, explosion proof housing.

Figure 2:
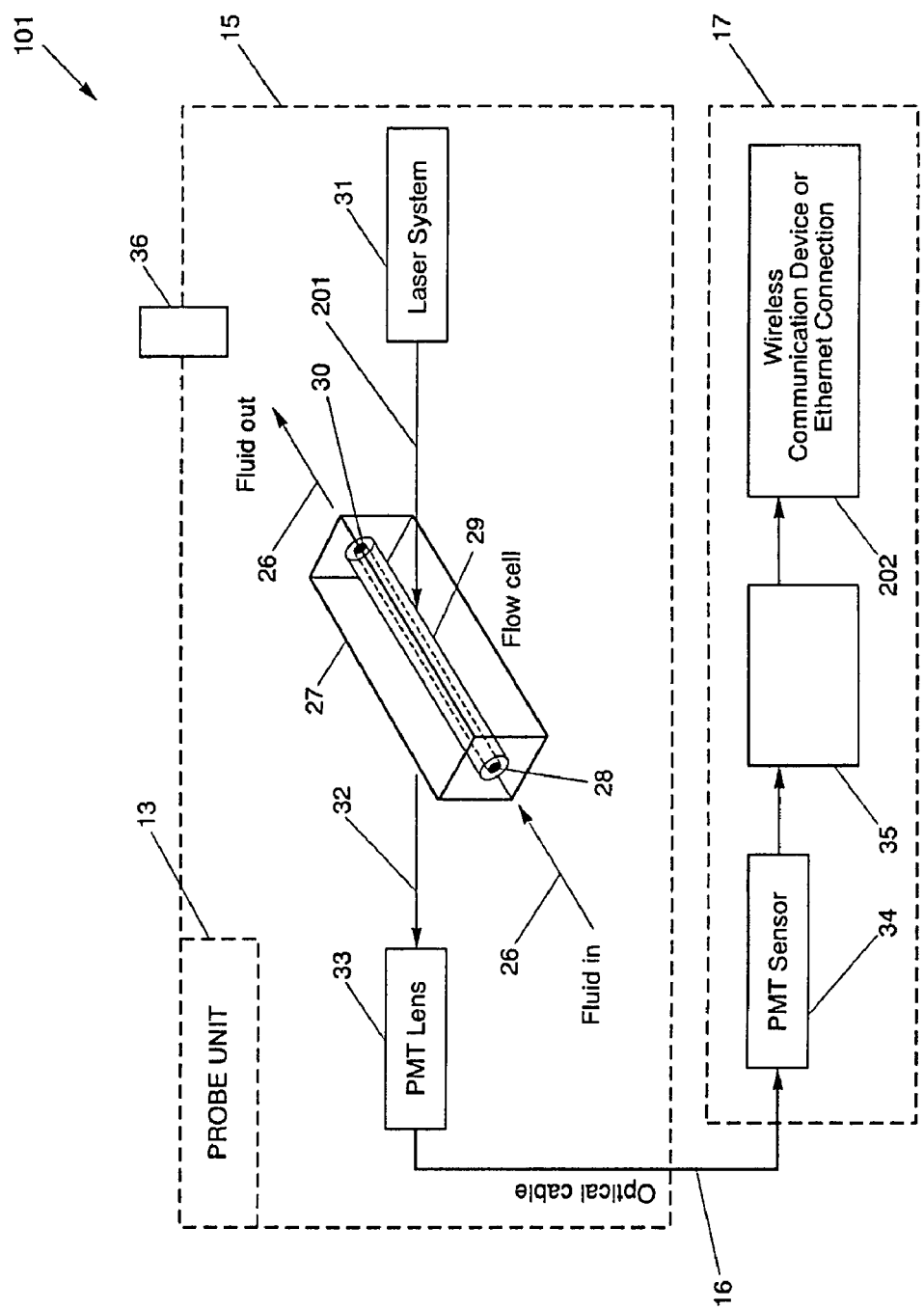
FIG. 2 illustrates functional components of an assembly for monitoring contaminants in a fluid flow in accordance with an embodiment of the present invention.

Referring now to FIG. 2, in an embodiment, analyzer 15 of monitor 101 can include a flow cell 27. In an embodiment, the flow cell 27 can be transparent. The flow cell 27 includes an inlet 28, an outlet 30, and a passageway 29 disposed therebetween. The flow cell 27 may be designed to receive the sampled fluid 26 from the probe 13 at inlet 28, which fluid can be permitted to progress through passageway 29, and exit at outlet 30. The passageway 29, in an embodiment, can serve as sampling space in which the sample fluid 26 can be illuminated by the light source 31 to identify contaminant particles.

Figure 3:
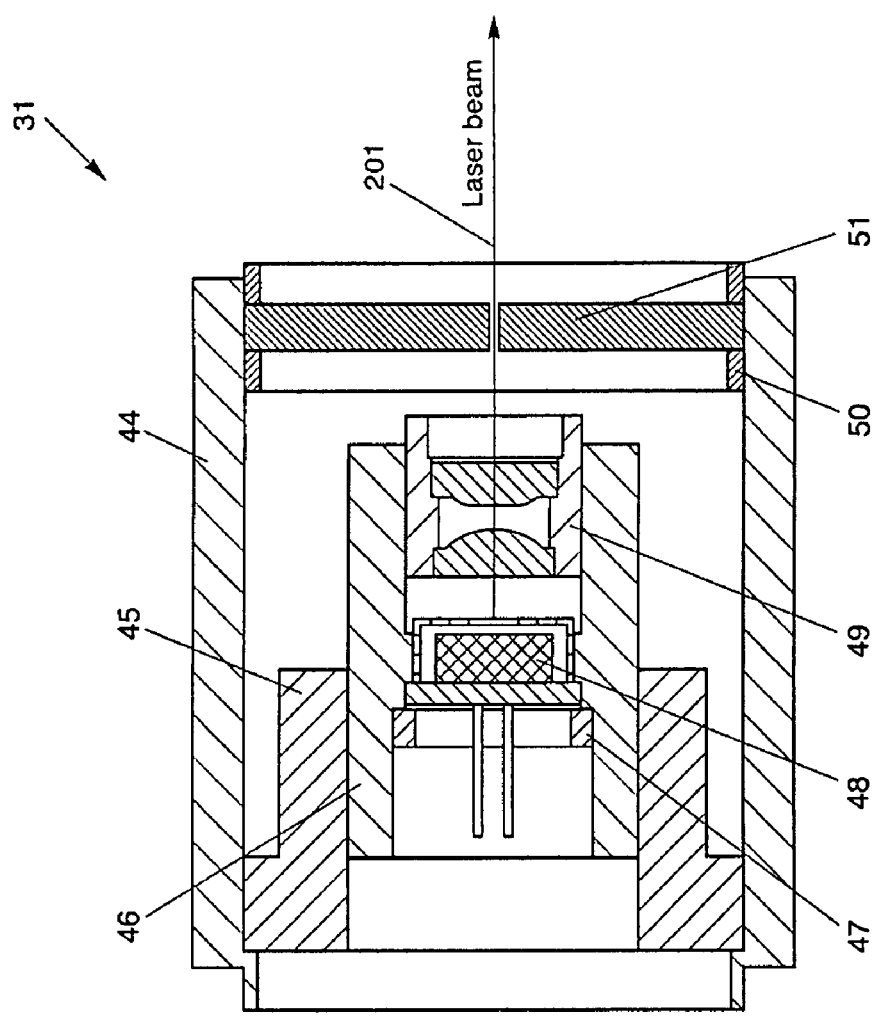
FIG. 3 illustrates a subassembly for use in connection with the system shown in FIG. 2.

Light source 31, in one embodiment, can be a laser system or other light source capable of generating a focused beam of light 201. The light source 31 can be designed to propagate a focused beam of light 201 towards a portion of the passageway 29 within the flow cell 27 containing the sampled fluid 26, such that scattered light can be generated when a contaminant particle in the sampled fluid 26 contacts the focused beam of light 201. In an embodiment shown in FIG. 3, light source 31 can include an infrared laser diode 48 that can emit laser radiation, for instance, at a wavelength of about 658 nanometers and about 50 mw of power. It should be appreciated that the wavelength and output power of the laser radiation can be designed to permit tuning or adjustment, for different applications. Light source 31 can further include a focus lens 49, which focuses the beam 201 emanating from the laser diode 48, and directs the beam 201 onto substantially the center of the flow cell 27. A spatial filter 51 can be included to reduce noise on the focused laser beam 201. Light source 31, in an embodiment, can also include 1) a lens tube 44 to hold the light source assembly together, 2) an adapter 45 for connecting the focus lens 49 to the lens tube 44, and 3) a focus lens tube 46 for holding the focus lens 49.

To accommodate light source 31, the flow cell 27, in an embodiment, can be tubular or rectangular in shape or any other geometric shape, and can be relatively transparent to light so that light from light source 31 can travel there through for subsequent analysis. To that end, the flow cell 27 can be made from a quartz material. Of course, other suitable materials can be used, for instance, glass, plastic, or sapphire, etc.

Figure 4:
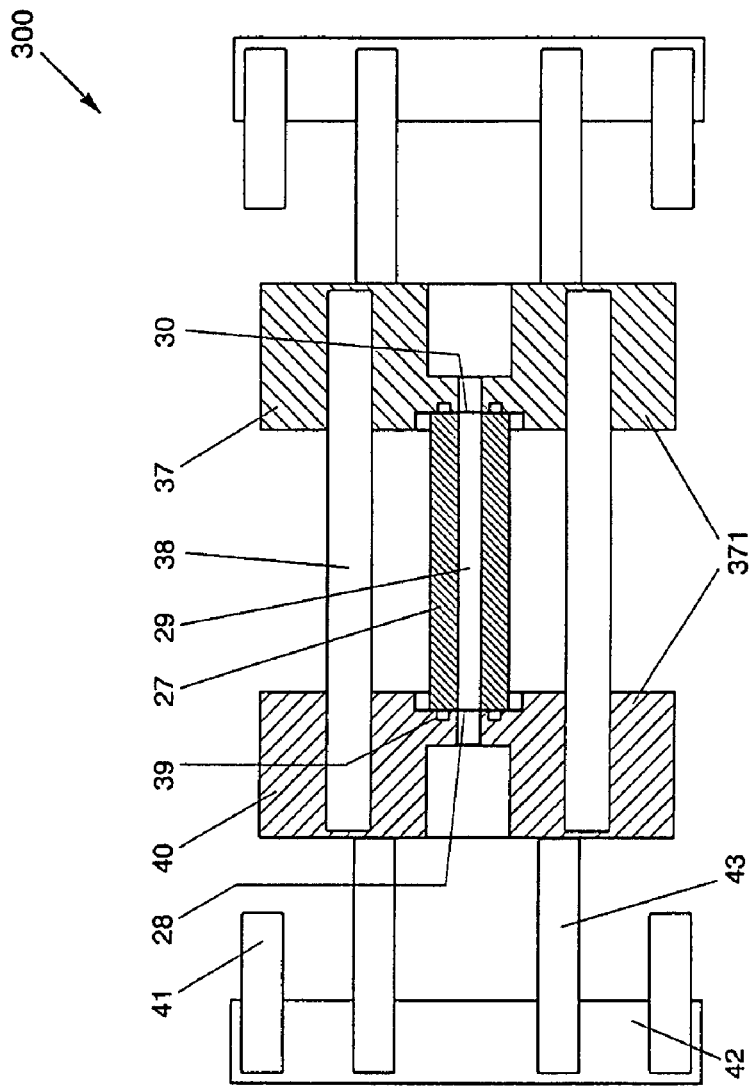
FIG. 4 illustrates a subassembly for use in connection with the system shown in FIG. 2.

To secure flow cell 27 in position, referring now to FIG. 4, a flow cell assembly 300 may be provided for high-pressure gas flow to be utilized. The assembly 300, in one embodiment, can include a base 37 upon which the flow cell 27 may be secured. In an embodiment, the base 37 may include two base ends 371 between which the flow cell 27 may be secured. Assembly 300 may also include connecting rods 38 for connecting the two base ends 371, and for pulling the base ends 371 toward one another to secure the flow cell 27 therebetween. In an embodiment, sealing gasket rings 39 can be utilized to prevent leakage of the sample fluid 26 from the flow cell 27. In addition, adapter plate 42 may be provided to hold the ends of base 37 in place, while connection rods 41, 43 can be utilized to secure the ends of base 37 to the adapter plate 42. It should be noted that assembly 300 and its component parts is simply one embodiment of an assembly mechanism for fastening and securing the flow cell 27 in proper position. Those skilled in the art will appreciate that various assembly mechanisms can be utilized to secure flow cell 27.

Figure 5:
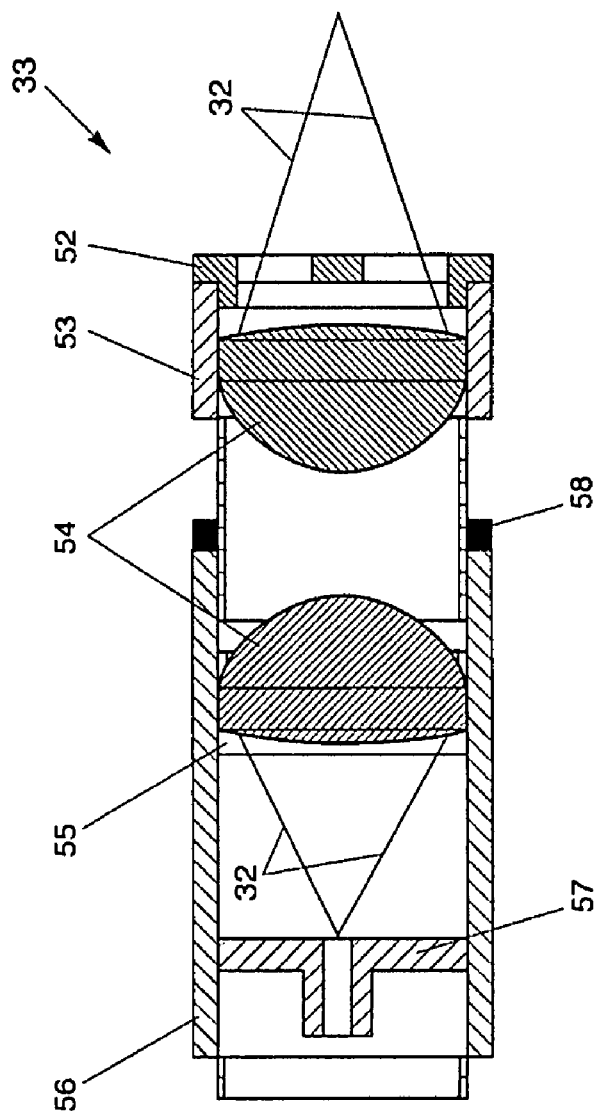
FIG. 5 illustrates a subassembly for use in connection with the system shown in FIG. 2.

Still referring to FIG. 2, the analyzer 15 can also include collecting lens assembly 33. Collecting lens assembly 33 may be designed to collect scattered light 32 emanating from the flow cell 27, and can direct the collected scattered light to a detector 34. In one embodiment, scattered light can be directed to detector 34 via fiber optic cable 16. Of course, the direction of scattered light to the detector 34 can be accomplished using other known mechanisms, which may not include the use of a fiber optic cable. Detector 34, in one embodiment, can be located in the processor assembly 17. As illustrated in FIG. 5, the collecting lens assembly 33 can include a light filter 52, lens system 54, and an optical cable adapter 57. The light filter 52, as shown, may be designed to block direct light, such as, incoming laser beam from the light source 31, but may be designed to allow scattered light 32 from the particles to pass through the filter 52. Scattered light passing through the filter 52, in an embodiment, can be collected by the lens system 54. Lens system 54, in one embodiment, can include opposing convex lenses designed to collect forward scattered light 32 from the particles. It should be noted that lens system 54 can have other configurations, for instance, one lens so long as that one lens has the properties of the two lens system. The collected scattered light can then be directed by lens system 54 to an optical sensor, such as detector 34, in processor assembly 17 via the fiber optic cable 16. In an embodiment, the fiber optic cable can act to reduce the scattered light to a optimum level of sensitivity for detector operation. In an embodiment, the fiber optic cable 16 can be connected to the collecting lens assembly 33 by the optical cable adapter 57. The collecting lens assembly 33 can also include a lens tube 56, which can have an adjustable tube portion 53 that houses the lens system 54. To secure the lens system 54 in place, retaining ring 55 may be provided to maintain the lens system 54 in the adjustable tube portion 53 of assembly 33. The adjustable tube 53 can be locked in place by a locking mechanism 58. Of course, other assemblies and mechanisms can be utilized to secure the lens system 54 in the proper position.

Figure 6:
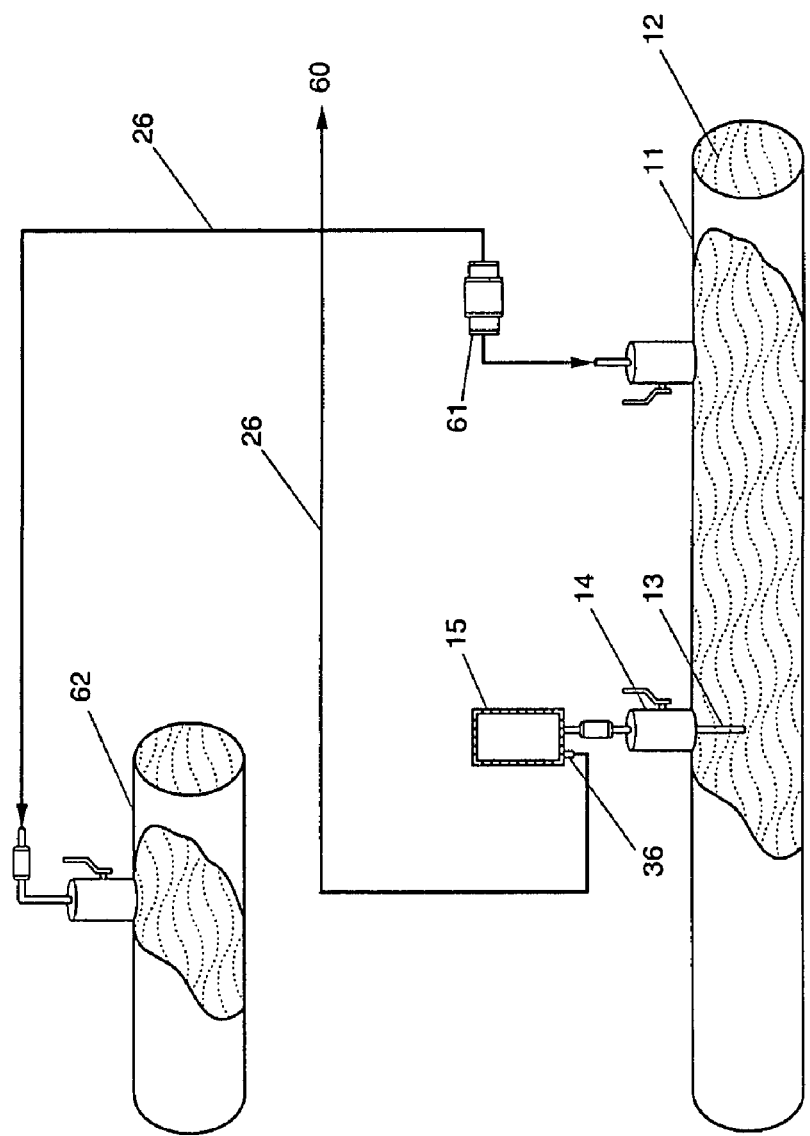
FIG. 6 illustrates various options for disposing of a contaminant sample once it has been processed in the assembly shown in FIG. 2.

With reference now to FIG. 6, in an embodiment, analyzer 15 of monitor 101 can also include a release valve 36, which can be utilized to control the flow rate, and to remove the analyzed sampled fluid 26 from the analyzer 15 when the sampled fluid 26 is no longer needed. After exiting the analyzer 15, there may be several options for disposal of the sampled fluid 26. In one option, the sampled fluid 26 may be reinjected back into pipeline 11 at high pressure, utilizing a high pressure gas pump 61 or compressor. In another option the sampled fluid 26 may be vented into the atmosphere 60. This option may be cost effective, but the sample amount vented may need to comply with greenhouse gas emissions requirements. A further option may be to direct the analyzed sampled fluid 26 into a low-pressure pipeline 62 or flare system.

Figure 7:
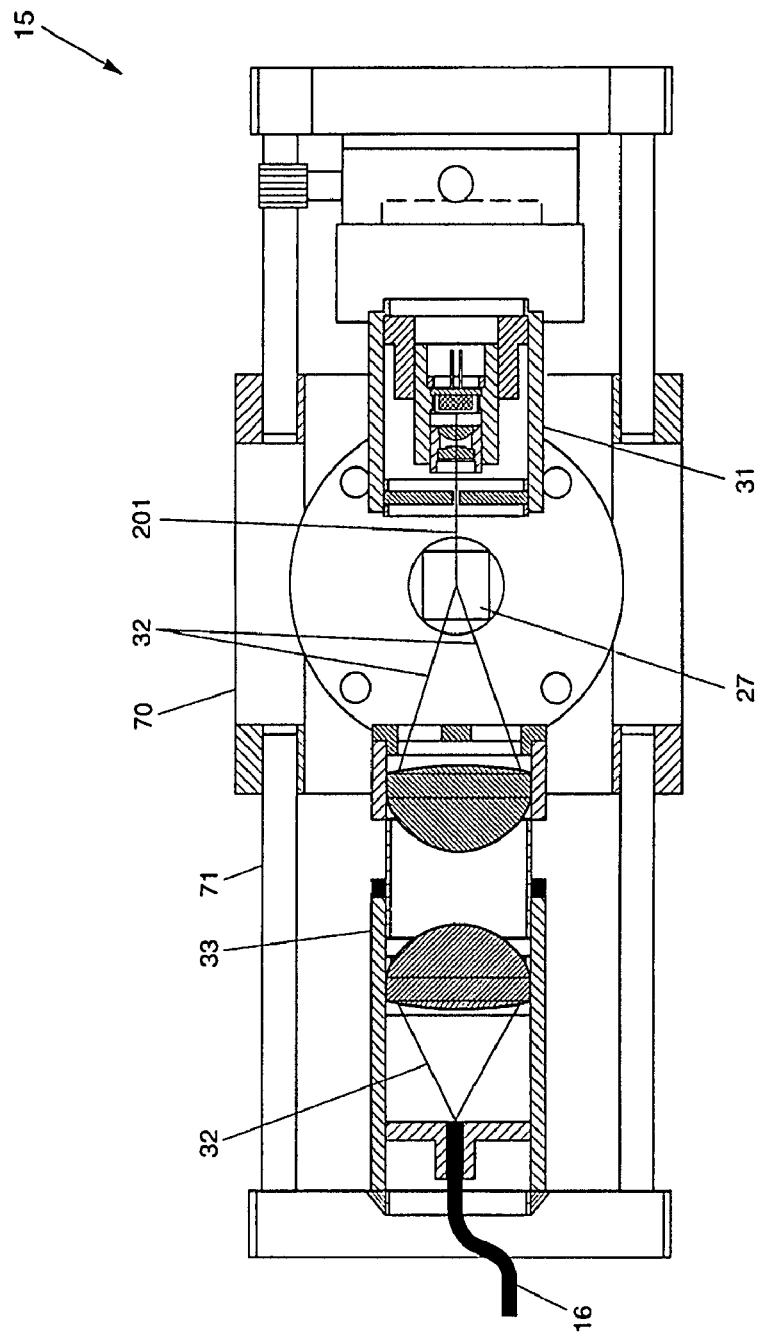
FIG. 7 illustrates an embodiment of the physical components, connections, and alignment of the assembly shown in FIG. 2.

FIG. 7 depicts an embodiment of an assembled analyzer 15 of monitor 101, and its components. As shown, the light source 31, flow cell 27, collecting lens assembly 33, and fiber optic cable 16, can be arranged in series within the analyzer 15. Of course, other designs may be used. To provide support and protection to the sub-assemblies and component parts, exterior case 70 and connection rods 71 may be provided.

Referring again to FIG. 2, as noted, monitor 101 can also include the processor assembly 17. In an embodiment, processor assembly 17, can be made to receive the scattered light from the collection lens assembly 33 in analyzer 15, convert the scattered light into data, and distribute the data over a communication network 22 to the central server 23. In one embodiment, the processor assembly 17 can include a detector 34. The detector 34 can be an optical sensor, such as a photomultiplier tube, photodiode, or charge-coupled device. The detector 34 can also receive scattered light from the collection lens assembly 33, and convert the scattered light into electrical signals that, in one embodiment, can be proportional to the size of contaminant particles in the sampled fluid 26. Various algorithms and commercially available technology can be used to accomplish this. As such, the intensity of the scattered light can be determined by the particle dimension and its refracting index. With such information, the particle size can be determined from the intensity of the scattered light.

The processor assembly 17 can also include processor 35, designed to receive the electrical signals from the detector 34. These signals can thereafter be quantified and converted into digital data pertaining to the contaminant particles. The digital data can include information such as particle size, contaminant concentration, and particle distribution. The processor 35, in an embodiment, can also distribute the digital data over the communication network 22, which can include the Internet, to the central server 23 for display and evaluation.

In an embodiment, the processor 35 can transfer the digital data to the central server 23, and/or communication network 22 via a wireless communication device 202, such as, a cell phone, satellite communication device, radio broadcast signal, or Ethernet connection. In one embodiment, the communication device 202 can be part of the processor assembly 17. Alternatively, the communication device 202 can be an external connection to the processor assembly 17.

In another embodiment, the processor 35 can transfer the digital data over a landline or network connection 18, 19 of system 10, to a LAN, such as an Ethernet hub, from which the data can then be accessed, by the central server 23 and/or client server 20 via the Internet or other communication network 22.

In addition, system 10 can include communication devices 24, 25, for example, cell phones, PDAs, etc. In an emergency situation, such as when contaminant levels are too high, cell phone 24 at the central server site can be utilized to call cell phone 25 to alert personnel at the client server site of the emergency.

Figure 8:
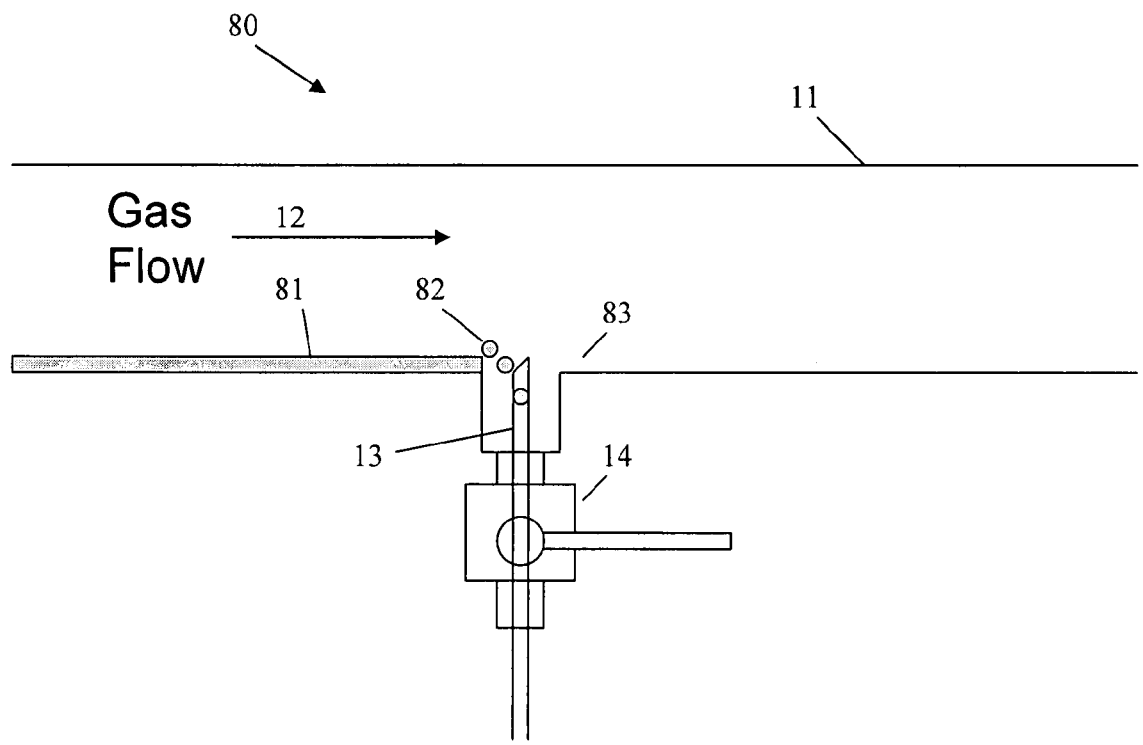
FIG. 8 illustrates a probe for use in connection with an embodiment of the present invention.

In another embodiment 80 illustrated in FIG. 8, the fluid flow 12 can be a low-pressure or high-pressure gas flow. Oftentimes, in gas flows, a liquid film 81 can form and travel along the inner surface 83 of the pipeline 11. Extending the probe 13 too far towards the middle of the pipeline 11, can result in proper sampling of the gaseous fluid flow 12, but can leave the liquid film 81 undetected. Proper positioning of the probe 13 within pipeline 11 can allow the probe 13 to sample aerosols, mist particles, and solid particles sufficiently small enough to be moved by or entrained in the gaseous fluid flow 12. For many types of fluid flows, the probe 13 can be positioned virtually anywhere in the pipeline 11, to acquire an accurate representative sample of the fluid flow 12. However, to sample the gaseous fluid flow 12 as well as the liquid film 81 traveling along the inner surface of the pipeline 11, the probe 13 can be minimally extended into the pipeline 11. For example, the probe 13 can be extended into the pipeline 11, and positioned so that the probe 13 does not extend beyond (or far beyond) inner surface 83 of the pipeline 11. The liquid film 81 can wick off the inner surface 83 of the pipeline 11, as mist and aerosol particles 82 that can be small enough to move with the gaseous fluid flow 12 into the probe 13 for subsequent detection and measurement.

In operation, with reference again to FIGS. 1 and 2, fluid flow 12 in pipeline 11 can be isokinetically sampled continuously or periodically by probe 13. The probe 13 can then direct the sampled fluid 26 to the analyzer 15 in the contaminant monitor 101. Upon entry into the analyzer 15, the sampled fluid 26 can be directed through the flow cell 27. The sample fluid 26 can enter the flow cell 27 at the inlet 28. As the sampled fluid 26 progresses through the passageway 29 in flow cell 27, it intersects and is illuminated by laser beam 201, which is generated by light source 31. The laser beam 201 can be aimed, in an embodiment, at approximately the center of flow cell 27.

In response to the illumination, illuminated contaminant particles in the sampled fluid 26 cause light 32 to scatter and emanate in various directions from flow cell 27. In one embodiment, the intensity of the scattered light can be determined by the particle dimension and its refracting index. Therefore, the particle size can be calculated from the intensity of the scattered light. The collection lens assembly 33 can then collect the forward scattered light 32, and direct it through the fiber optic cable 16, out of analyzer 15, and to detector 34 located in the processor assembly 17 for further processing. Also, once the sampled fluid 26 exits the flow cell 27 at outlet 30, it may no longer be needed, and can be released from the analyzer 15 through release valve 36.

The detector 34, in an embodiment, can include a photomultiplier tube, photodiode, or both, can be located in the processing assembly 17, and can receive the scattered light from the fiber optic cable 16. The detector 34 acts to convert the scattered light, in one embodiment, into modular electrical signals that can be proportional to the size of the contaminant particles. The detector 34 can then transfer the electrical signal to the processor 35, which can quantify and convert the electrical signals into digital data pertaining to the contaminant particles. The digital data can include particle size, contaminant concentration, and particle distribution data. The digital data can subsequently be utilized to determine if the level of contaminants is above an acceptable threshold level. In an embodiment, particle sizes ranging from 0.1 microns to 100 microns can be identified.

Thereafter, the processor 35 can utilize an Ethernet connection or wireless communication device to form a connection link 19, to the client server 20, in order to transmit digital data directly to the client server 20 for display and evaluation. In one embodiment of the present invention, the digital data can be transmitted simultaneously to the remotely located central server 23 via link 18 and network 22. In addition to transmitting digital data to the client server 20 and the central server 23, notification of alerts and emergency conditions can also be sent.

In another embodiment, there may be no direct communication link 19 between the contaminant monitor 101 and the client server 20. In such a configuration, the digital data can be transmitted over communication link 18, across network 22, and on to central server 23. The central server 23 can then evaluate the digital data to determine the contaminant levels in pipelines 11, and if necessary, update the various client servers 20 with reports that may be transmitted over the Internet 22 and communication link 21. Similarly, the central server 23 can notify and alert the client servers 20 of emergency conditions, for instance, if contaminant threshold levels have increased to unsafe levels.

The present invention can be utilized in critical containment-sensitive applications, such as, power generation and ultrasonic gas metering, etc. The present invention can be utilized to provide a customer/client with an indication as to when downstream equipment may be in danger of being harmed by high contaminant levels in pipelines. The present invention can also be implemented as a service that provides customers with contaminant level updates, as well as immediate alerts in the event of a drastic increase in contaminant levels.

Advantages of the present invention include the ability to remotely and continuously monitor contaminant levels in multiple pipelines, and at multiple sites from a single central server. Another advantage of the present invention is the ability to quickly respond, and provide notification of sudden increased contamination levels at client sites, in order to prevent equipment damage at the client site.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains.

What is claimed is:

1. A pipeline contaminant monitor comprising:
    a housing;
    an analyzer, situated within the housing, for (a) illuminating, with a light source, sampled fluid removed from a pipeline having contaminant particles, and (b) collecting, from contaminant particles in the illuminated sampled fluid, scattered light generated from size, distribution and concentration of the contaminant particles in the sampled fluid, the analyzer having a flow cell configured to receive sampled fluid flow at pressure and temperature within the pipeline and to preserve the sampled fluid flow at pressure and temperature within the pipeline, so as to accurately maintain the size, distribution and concentration of the contaminant particles therewithin for subsequent measurement;
    at least one detector, situated within the housing, for generating electrical signals from the scattered light from the analyzer; and
    a processor, situated within the housing, for a) converting the electrical signals from the detector into digital data pertaining to the contaminant particles for evaluation, and b) distributing the digital data via a communication network to at least one digital data processor for further processing.

2. A pipeline contaminant monitor according to claim 1, further comprising a probe for extending into the pipeline for isokinetically sampling fluid in the pipeline to ensure that a representative amount of contaminants within the pipeline can subsequently be measured.

3. A pipeline contaminant monitor according to claim 2, further comprising a pump for re-injecting the sampled fluid into the pipeline.

4. A pipeline contaminant monitor according to claim 2, wherein the fluid in the pipeline is a high-pressure gas flow.

5. A pipeline contaminant monitor according to claim 2, wherein the probe has a substantially uniform diameter for isokinetically sampling fluid in the pipeline.

6. A pipeline contaminant monitor according to claim 1, further comprising a probe for extending into the pipeline for non-isokinetically sampling fluid in the pipeline.

7. A pipeline contaminant monitor according to claim 1, further comprising a probe for minimally extending into the pipeline for sampling fluid located along an inner surface of the pipeline.

8. A pipeline contaminant monitor according to claim 1, wherein the flow cell has an inlet, an outlet, and a passageway therebetween, the flow cell designed to receive the sampled fluid at the inlet, and directing the sampled fluid through the passageway so as to permit the fluid to be illuminated by the light source, and the outlet.

9. A pipeline contaminant monitor according to claim 1, wherein the analyzer further includes a collection lens for collecting the scattered light and transferring the scattered light to a detector for further processing.

10. A pipeline contaminant monitor according to claim 1, wherein the fluid in the pipeline is a high-pressure fluid flow.

11. A pipeline contaminant monitor according to claim 1, wherein the fluid in the pipeline is a low-pressure fluid flow.

12. A pipeline contaminant monitor according to claim 1, wherein the light source is a laser diode.

13. A pipeline contaminant monitor according to claim 1, wherein the detector is a photomultiplier tube, photodiode, or charge-coupled device.

14. A pipeline contaminant monitor according to claim 1, wherein the digital data includes particle distribution, particle size data, and contaminant concentration.

15. A pipeline contaminant monitor according to claim 1, wherein the analyzer is designed to collect scattered light from liquid aerosol contaminant particles having a size of about 0.1 microns to about 10 microns.

16. A pipeline contaminant monitor according to claim 1, wherein the analyzer is designed to collect scattered light from liquid mist contaminant particles having a size of about 11 microns to about 100 microns.

17. A pipeline contaminant monitor according to claim 1, wherein the analyzer is designed to collect scattered light from liquid, aerosol, and solid contaminant particles.

18. A pipeline contaminant monitor according to claim 1, wherein the processor is designed to transmit digital data to the communication network on an Ethernet connection.

19. A pipeline contaminant monitor according to claim 1, wherein the processor is designed to transmit digital data over a wireless communication network.

20. A pipeline contaminant monitor according to claim 1, further comprising a fiber optic cable for directing the scattered light to the detector.

21. A pipeline contaminant monitor according to claim 20, wherein the fiber optic cable acts to reduce the scattered light to a level for optimum sensitivity and detector operation.

22. A pipeline contaminant monitor according to claim 1, wherein the monitor is configured to monitor solid particles in a fluid.

23. A pipeline contaminant monitor according to claim 1, wherein the monitor is configured to monitor the presence of water droplets in a fluid.

24. A pipeline contaminant monitor according to claim 1, wherein the monitor is configured to identify levels of contaminants to determine whether maintenance within the pipeline is required.

25. A method of monitoring contaminants in a pipeline, the method comprising:
   directing a sample of a fluid flow removed from a pipeline into a device for monitoring contaminant particles, such that the fluid sample along with contaminant particles therewithin are preserved at pressure and temperature existing within the pipeline, so as to accurately maintain particle size, distribution and concentration for subsequent measurement;
   illuminating, within the device, the sampled fluid from a pipeline with a light source, so as to generate scattered light from the size, distribution and concentration of the contaminant particles within the sample;
   converting the scattered light into an electrical signal that is representative of the contaminant particle size;
   processing the electrical signal into digital data pertaining to the contaminant particles; and
   transmitting the digital data via a communication network to a remotely situated digital data processor for evaluation.

26. A method as set forth in claim 25, further comprising the step of non-isokinetically sampling the fluid in the pipeline.

27. A method as set forth in claim 25, further comprising the step of isokinetically sampling the fluid in the pipeline.

28. A method as set forth in claim 27, further comprising the step of re-injecting the sampled fluid into the pipeline.

29. A method as set forth in claim 25, further comprising the step of venting the sampled fluid into the atmosphere.

30. A method as set forth in claim 25, further comprising the step of storing the digital data pertaining to the contaminant particles for reference and comparison.

31. A method as set forth in claim 25, wherein the step of illuminating includes inserting a probe into the pipeline for isokinetically sampling fluid in the pipeline to ensure that a representative amount of contaminants within the pipeline can subsequently be measured.

32. A method as set forth in claim 25, wherein the step of illuminating includes directing the sampled fluid through a flow cell so as to permit at least one contaminant particle in the sampled fluid to contact with light from the light source to generate scattered light.

33. A method as set forth in claim 25, wherein the step of distributing includes transmitting the digital data to the communication network on an Ethernet connection.

34. A method as set forth in claim 25, wherein the step of distributing includes transmitting the digital data over a wireless communication network or broadcast signal.

35. A pipeline contaminant monitor comprising:
   a housing independent of a pipeline;
   a flow cell positioned within a housing and having an inlet, an outlet, and a passageway therebetween, the flow cell designed to receive at the inlet sampled fluid removed from the pipeline at pressure and temperature within the pipeline, to preserve the sampled fluid along with contaminant particles therein at pressure and temperature within the pipeline, so as to accurately maintain size, distribution and concentration of the contaminant particles at such conditions existing in the pipeline, and to direct the sampled fluid through the passageway and the outlet;
   a light source, positioned within the housing, for propagating a beam of light across the passageway containing the sampled fluid, so that scattered light is generated from size, distribution and concentration of the contaminant particles when the contaminant particles contact the focused beam; and
   a collection lens for collecting the scattered light and transferring the scattered light to a detector for further processing.

36. A pipeline contaminant monitor according to claim 35, further comprising a probe for extending into the pipeline for isokinetically sampling fluid in the pipeline to ensure that a representative amount of contaminant particles within the pipeline can subsequently be measured.

37. A pipeline contaminant monitor according to claim 35, wherein the light source is a laser diode.

38. A pipeline contaminant monitor according to claim 35, further comprising:
   at least one detector for converting the scattered light received from the collection lens into an electrical signal that is proportional to the contaminant particles size; and
   a processor for generating digital data from the electrical signal received from the detector, and distributing the digital data via a communication network to at least one digital data processor, remotely situated from the pipeline, for display and evaluation.

39. A pipeline contaminant monitor according to claim 38, wherein the processor transmits the digital data to the communication network on an Ethernet connection.

40. A pipeline contaminant monitor according to claim 38, wherein the processor transmits the digital data over a wireless communication network or on a broadcast signal.

41. A pipeline contaminant monitor comprising:
   a housing;
   an analyzer, situated within the housing, for (a) illuminating, with a light source, sampled fluid from a pipeline having contaminant particles, and (b) collecting, from contaminant particles in the illuminated sampled fluid, scattered light generated from size, distribution and concentration of the contaminant particles in the sampled fluid, the analyzer having a flow cell configured to receive sampled fluid flow at pressure and temperature within the pipeline and to preserve the sampled fluid flow at pressure and temperature within the pipeline, so as to accurately maintain the size, distribution and concentration of the contaminant particles therewithin for subsequent measurement;

a filter in the housing and adjacent the light source, the filter designed to block direct light from the light source and allow scattered light from the contaminant particles to pass through;

at least one detector, in the housing, for generating electrical signals from the scattered light from the analyzer; and a processor, in the housing, for a) converting the electrical signals from the detector into digital data pertaining to the contaminant particles for evaluation, and b) distributing the digital data via a communication network to at least one digital data processor for further processing.

42. A method of monitoring contaminants in a pipeline, the method comprising:

directing a sample of a fluid flow from a pipeline into a device for monitoring contaminant particles, such that the fluid sample along with contaminant particles therewithin are preserved at pressure and temperature existing within the pipeline, so as to accurately maintain particle size, distribution and concentration;

illuminating, within the device, the sampled fluid from a pipeline with a light source, so as to generate scattered light from the size, distribution and concentration of the contaminant particles within the sample;

filtering direct light from the light source and allowing scattered light from the particles to pass through;

converting the scattered light into an electrical signal that is representative of the contaminant particle size;

processing the electrical signal into digital data pertaining to the contaminant particles; and transmitting the digital data via a communication network to a remotely situated digital data processor for evaluation.

43. A pipeline contaminant monitor comprising:

a housing independent of a pipeline;

a flow cell positioned within a housing and having an inlet, an outlet, and a passageway therebetween, the flow cell designed to receive at the inlet sampled fluid at pressure and temperature within a pipeline, to preserve the sampled fluid along with contaminant particles therein at pressure and temperature within the pipeline, so as to accurately maintain size, distribution and concentration of the contaminant particles at such conditions existing in the pipeline, and to direct the sampled fluid through the passageway and the outlet;

a light source, positioned within the housing, for propagating a beam of light across the passageway containing the sampled fluid, so that scattered light is generated from size, distribution and concentration of the contaminant particles when the contaminant particles contact the focused beam;

a filter designed to block direct light from the light source and allow scattered light from the particles to pass through; and a collection lens for collecting the scattered light and transferring the scattered light to a detector for further processing.

* * * * *